(12) United States Patent
Jones

(10) Patent No.: US 9,795,561 B2
(45) Date of Patent: Oct. 24, 2017

(54) COMBINATION OF UMECLIDINIUM, FLUTICASONE PROPIONATE AND SALMETEROL XINAFOATE FOR USE IN THE TREATMENT OF INFLAMMATORY OR RESPIRATORY TRACT DISEASES

(71) Applicant: Glaxo Group Limited, Brentford, Middlesex (GB)

(72) Inventor: Christine Elaine Jones, Research Triangle Park, NC (US)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 14/651,988

(22) PCT Filed: Dec. 17, 2013

(86) PCT No.: PCT/EP2013/076978
§ 371 (c)(1),
(2) Date: Jun. 12, 2015

(87) PCT Pub. No.: WO2014/095924
PCT Pub. Date: Jun. 26, 2014

(65) Prior Publication Data
US 2015/0313841 A1    Nov. 5, 2015

(30) Foreign Application Priority Data

Dec. 17, 2012 (GB) .................................. 1222679.1

(51) Int. Cl.
| | |
|---|---|
| A61K 31/569 | (2006.01) |
| A61K 47/26 | (2006.01) |
| A61K 31/137 | (2006.01) |
| A61K 31/439 | (2006.01) |
| A61K 31/56 | (2006.01) |
| A61K 9/00 | (2006.01) |
| A61J 1/03 | (2006.01) |

(52) U.S. Cl.
CPC ............. *A61K 9/0075* (2013.01); *A61J 1/035* (2013.01); *A61K 31/137* (2013.01); *A61K 31/439* (2013.01); *A61K 31/56* (2013.01); *A61K 31/569* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 6,537,983 B1 | 3/2003 | Biggadike et al. | |
| 6,759,398 B2 | 7/2004 | Biggadike | |
| 6,878,698 B2 | 4/2005 | Biggadike et al. | |
| 7,101,866 B2 | 9/2006 | Biggadike et al. | |
| 7,361,787 B2 | 4/2008 | Box et al. | |
| 7,439,393 B2 | 10/2008 | Box et al. | |
| 7,488,827 B2 | 2/2009 | Laine et al. | |
| 7,498,440 B2 | 3/2009 | Laine et al. | |
| 7,629,335 B2 | 12/2009 | Biggadike et al. | |
| 7,776,895 B2 | 8/2010 | Box et al. | |
| 7,982,067 B2 | 7/2011 | Box et al. | |
| 8,183,257 B2 | 5/2012 | Laine et al. | |
| 8,309,572 B2 | 11/2012 | Laine et al. | |
| RE44,874 E | 4/2014 | Box et al. | |
| 2009/0029901 A1 | 1/2009 | Wood-Kaczmar et al. .................. | 536/123.13 |
| 2009/0298742 A1 | 12/2009 | Roche et al. ................ | 536/1.11 |
| 2011/0269970 A1 | 11/2011 | Box et al. | |
| 2012/0309725 A1 | 12/2012 | Baker et al. | |
| 2014/0113888 A1 | 4/2014 | Crater | |
| 2016/0095840 A1 | 4/2016 | Baker et al. | |

FOREIGN PATENT DOCUMENTS

| | | |
|---|---|---|
| WO | 2003024439 A1 | 3/2003 |
| WO | 2004110404 A1 | 12/2004 |
| WO | 2005037280 A1 | 4/2005 |
| WO | 2005046636 A1 | 5/2005 |
| WO | 2005104745 A2 | 11/2005 |
| WO | 2005115463 A1 | 12/2005 |
| WO | WO2005/115462 | 12/2005 |
| WO | WO2005/115464 | 12/2005 |
| WO | WO2005/115465 | 12/2005 |
| WO | WO2005/115466 | 12/2005 |
| WO | WO2005/115467 | 12/2005 |
| WO | 2006062883 A2 | 6/2006 |
| WO | 2006062931 A2 | 6/2006 |
| WO | 2007012871 A1 | 2/2007 |
| WO | 2007068896 A1 | 6/2007 |
| WO | 2008012338 A2 | 1/2008 |
| WO | 2008021142 A2 | 2/2008 |
| WO | 2009036243 A1 | 3/2009 |
| WO | 2010038086 A2 | 4/2010 |
| WO | 2010072354 A1 | 7/2010 |

(Continued)

OTHER PUBLICATIONS

Barnes; "Triple inhalers for obstructive airways disease: Will they be useful?"; Expert Review of Respiratory Medicine, Expert Reviews; 2011; vol. 5, No. 3; pp. 297-300.
Cazzola et al.; "The scientific rationale for combining long-acting beta2-agonists and muscarinic antagonists in COPD"; Pulmonary Pharmacology & Therapeutics ; 2010; vol. 23, No. 4; pp. 257-267.
Laine et al.; "Discovery of Novel 1-Azoniabicyclo [2.2.2] octane Muscarinic Acetylcholine Receptor Antagonists"; Journal of Medicinal Chemistry; 2009; vol. 52, No. 8; pp. 2493-2505.
Aaron et al., Tiotropium in combination with placebo, salmeterol, or fluticasone-salmeterol for treatment of chronic obstructive pulmonary disease: a randomized trial. Ann Intern Med. Apr. 17, 2007;146(8):545-55.

(Continued)

*Primary Examiner* — Samantha Shterengarts
(74) *Attorney, Agent, or Firm* — James P. Riek; R. Steve Thomas; William R. Majarian

(57) ABSTRACT

The present invention is directed to pharmaceutical combination products comprising a muscarinic acetylcholine receptor antagonist, fluticasone propionate and salmeterol xinafoate, and to their use in the treatment of inflammatory or respiratory tract diseases.

21 Claims, No Drawings

(56) References Cited

FOREIGN PATENT DOCUMENTS

| WO | 2010097114 A1 | 9/2010 |
|---|---|---|
| WO | 2010097115 A1 | 9/2010 |
| WO | 2011067212 A1 | 6/2011 |
| WO | 2012168160 A1 | 12/2012 |
| WO | 2012168161 A1 | 12/2012 |

OTHER PUBLICATIONS

Allen et al., Fluticasone Furoate (FF) A Novel Inhaled Corticosteroid (ICS) Demonstrates Prolonged Lung Absorption Kinetics in Man. American Thoracic Society 2010 International Conference, Abstract D21 Asthma Therapy: New Targets, New Tricks. DOI: http://dx.doi.org/10.1164/ajrccm-conference.2010.181.1_MeetingAbstracts.A5408 (2010).
Allen et al., Fluticasone furoate, a novel inhaled corticosteroid, demonstrates prolonged lung absorption kinetics in man compared with inhaled fluticasone propionate. Clin Pharmacokinet. Jan. 2013;52(1):37-42.
Biggadike, Fluticasone furoate/fluticasone propionate—different drugs with different properties. Clin Respir J. Jul. 2011;5(3):183-4.
Donohue et al., Efficacy and safety of once-daily umeclidinium/vilanterol 62.5/25 mcg in COPD. Respir Med. Oct. 2013;107(10):1538-46.
Donohue et al., Magnitude of umeclidinium/vilanterol lung function effect depends on monotherapy responses: Results from two randomised controlled trials. Respir Med. Mar. 2016;112:65-74.
Eklira Genuair 322 micrograms inhalation powder, Summary of Product Characteristics.
FDA, U.S. Food & Drug Administration, Tudorza™Pressair™—US FDA Approved Product Label. Retrieved online at: http://www.accessdata.fda.gov/scripts/cder/daf/index.cfm?event=BasicSearch.process (2012).
Fluticasone, www.Drugs.com, Wolters Kluwer Health (Wayback) (Jun. 4, 2009).
Forest Pharmaceuticals, Highlights of Prescribing Information, Tudorza Pressair. (2012).
GlaxoSmithKline, Evaluate the Safety, Efficacy and Dose Response of GSK573719 in Combination With Fluticasone Furoate in Subjects With Asthma (ILA115938). ClinicalTrials.gov Identifier NCT01573624, First Received Apr. 5, 2012, retrieved online at: https://clinicaltrials.gov/ct2/show/NCT01573624.
Glaxosmithkline, Highlights of Prescribing Information, Anoro Ellipta, FDA NDA 203975s003. (2016).
GSK Annual Report, retrieved online at: http://annualreport.gsk.com/ (2015).
Jones, Aclidinium bromide twice daily for the treatment of chronic obstructive pulmonary disease: a review. Adv Ther. Apr. 2013;30(4):354-68.
Laine et al., the pre-clinical pharmacology of the inhaled muscarinic antagonist GSK573719 predicts once-daily clinical dosing. European Respiratory Journal, 2011; 38(Suppl 55):3450.
Peters et al., Tiotropium bromide step-up therapy for adults with uncontrolled asthma. N Engl J Med. Oct. 28, 2010;363(18):1715-26.
Rosebraugh, Center for Drug Evaluation and Research, Approval Package for: Application No. 203975. Dec. 18, 2013.
Schelfhout et al., Activity of aclidinium bromide, a new long-acting muscarinic antagonist: a phase I study. Br J Clin Pharmacol. May 2010;69(5):458-64.
Welte et al., Efficacy and tolerability of budesonide/formoterol added to tiotropium in patients with chronic obstructive pulmonary disease. Am J Respir Crit Care Med. Oct. 15. 2009;180(8):741-50.
World Health Organization, The top 10 causes of death. WHO Fact Sheet No. 310, retrieved online at: http://www.who.nt/mediacentre/factsheets/fs310/en/, Updated May 2014.
Response filed Apr. 14, 2015 to U.S. Office Action for U.S. Appl. No. 13/510,962, dated Jan. 14, 2015.
Response filed Aug. 20, 2014 to U.S. Office Action for U.S. Appl. No. 13/510,962, dated Jun. 20, 2014.
Response filed Jun. 10, 2016 to U.S. Office Action for U.S. Appl. No. 14/970,945, dated Feb. 12, 2016.
Response filed Jun. 21, 2013 to U.S. Office Action for U.S. Appl. No. 13/510,962, dated Jun. 10, 2013.
Response filed Mar. 10, 2014 to U.S. Office Action for U.S. Appl. No. 13/510,962, dated Oct. 9, 2013.
Response filed May 2, 2016 to U.S. Office Action for U.S. Appl. No. 14/124,276, dated Feb. 2, 2016.
Response filed Oct. 24, 2016 to U.S. Office Action for U.S. Appl. No. 14/970,945, dated Aug. 24, 2016.
U.S. Notice of Allowance for U.S. Appl. No. 14/970,945, dated Jan. 11, 2017.
U.S. Office Action for U.S. Appl. No. 13/510,962, dated Jan. 14, 2015.
U.S. Office Action for U.S. Appl. No. 13/510,962, dated Jun. 10, 2013.
U.S. Office Action for U.S. Appl. No. 13/510,962, dated Jun. 16, 2015.
U.S. Office Action for U.S. Appl. No. 13/510,962, dated Jun. 20, 2014.
U.S. Office Action for U.S. Appl. No. 13/510,962, dated Oct. 9, 2013.
U.S. Office Action for U.S. Appl. No. 14/124,276, dated Feb. 2, 2016.
U.S. Office Action for U.S. Appl. No. 14/124,276, dated Jul. 6, 2016.
U.S. Office Action for U.S. Appl. No. 14/970,945, dated Aug. 24, 2016.
U.S. Office Action for U.S. Appl. No. 14/970,945, dated Feb. 12, 2016.
U.S. Appl. No. 12/353,436, filed Jan. 14, 2009, Muscarinic Acetylcholine Receptor Antagonists.
U.S. Appl. No. 13/401,890, filed Feb. 22, 2012, Muscarinic Acetylcholine Receptor Antagonists.
U.S. Appl. No. 13/510,962, filed Aug. 20, 2012, Combinations of a Muscarinic Receptor Antagonist and a Beta-2 Adrenoreceptor Agonist.
U.S. Appl. No. 14/970,945, filed Dec. 16, 2015, Combinations of A Muscarinic Receptor Antagonist and a Beta-2 Adrenoreceptor Agonist.
Jones et al., Efficacy and safety of once-daily aclidinium in chronic obstructive pulmonary disease, Respiratory Research (2011), 12:55 http://respiratory-research.com/content/12/1/55.
FDA Pulmonary Allergy Drugs Advisory Committee Meeting, Feb. 23, 2012, NDA 202-450: aclidinium bromide for the long-term, maintenance treatment of bronchospasm associated with chronic obstructive pulmonary disease (COPD), including chronic bronchitis and emphysema. (UMC292620). Retrieved from: https://www.fda.gov/downloads/AdvisoryCommittees/CommitteesMeeting-Materials/Drugs/Pulmonary-AllergyDrugsAdvisoryCommittee/UCM292620.pdf.
Donohue et al., A randomized, double-blind dose-ranging study of the novel LAMA GSK573719 in patients with COPD. Respir Med. Jul. 2012;106(7):970-9.

COMBINATION OF UMECLIDINIUM, FLUTICASONE PROPIONATE AND SALMETEROL XINAFOATE FOR USE IN THE TREATMENT OF INFLAMMATORY OR RESPIRATORY TRACT DISEASES

This application is filed pursuant to 35 U.S.C. §371 as a United States National Phase Application of International Patent Application No. PCT/EP2013/076978 filed Dec. 17, 2013, which claims priority from Great Britain Application No. 1222679.1 filed in the United Kingdom on Dec. 17, 2012.

FIELD OF THE INVENTION

This invention relates to pharmaceutical combination products for use in the treatment of inflammatory or respiratory tract diseases. More particularly, this invention relates to the combination of a muscarinic receptor antagonist, a corticosteroid (fluticasone propionate) and a beta-2 adrenoreceptor agonist (salmeterol xinafoate) for the treatment of COPD and/or asthma.

BACKGROUND OF THE INVENTION

Chronic obstructive pulmonary disease (COPD) is a chronic respiratory disorder that affects approximately 3 million people in the UK alone. COPD is one of the most common respiratory disorders and a leading cause of death worldwide. The disorder usually affects people over the age of 35, although a significant percentage of sufferers are not diagnosed until they are in their fifties. It is characterised by airflow obstruction that is not fully reversible and typical symptoms include exertional breathlessness, persistant cough and frequent chest infections. The primary cause of COPD is smoking.

There is currently no cure for COPD, however, progress of the disease may be slowed by treatment and by making lifestyle changes. Available forms of treatment include inhaled therapy, oral therapy, combined oral and inhaled therapy, oxygen therapy, lung surgery and vaccination and anti-viral therapy.

Asthma is a chronic inflammatory disorder of the airways, which affects approximately 300 million people worldwide. The disorder is characterised by widespread, variable and reversible airflow obstruction, and asthmatic patients typically experience episodes of breathlessness, chest tightness, wheezing and coughing. Corticosteroid monotherapy and combination therapy with a LABA have become established methods for the maintenance treatment of asthma.

Despite the treatment options currently available, there exists a need for alternative therapies for the effective management of respiratory diseases, such as COPD and asthma. In particular, there exists a need for management of those patients that are currently poorly controlled on any approved and recommended treatment plan.

SUMMARY OF THE INVENTION

In a first aspect the present invention provides a pharmaceutical combination product comprising:

a) a compound of the formula:

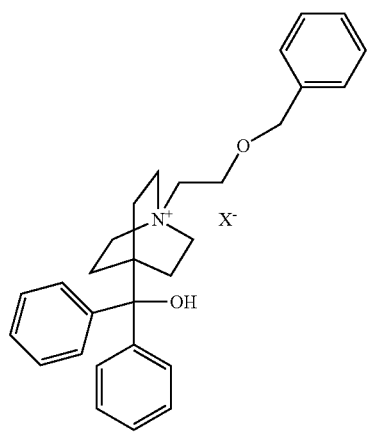

Compound (I)

wherein
X⁻ is a pharmaceutically acceptable anion;
b) fluticasone propionate; and
c) salmeterol xinafoate.

In one embodiment, the pharmaceutical combination product comprises 4-[hydroxy(diphenyl)methyl]-1-{2-[(phenylmethyl)oxy]ethyl}-1-azoniabicyclo[2.2.2]octane bromide, which is referred to hereinafter as umeclidinium bromide.

In a second aspect, this invention also provides pharmaceutical combination products for use in therapy, particularly for use in the treatment of inflammatory or respiratory tract diseases, such as asthma or COPD.

In a third aspect of the invention is a method for the treatment of an inflammatory or respiratory tract disease, such as asthma of COPD, comprising administering to a patient in need thereof a therapeutically effective amount of a product of the present invention.

DETAILED DESCRIPTION OF THE INVENTION

The present invention is directed to a pharmaceutical combination product comprising
a) a compound of the formula:

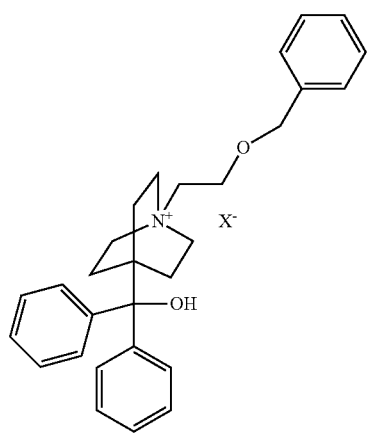

Compound (I)

wherein

X⁻ is a pharmaceutically acceptable anion;

b) fluticasone propionate; and c) salmeterol xinafoate.

The pharmaceutically acceptable anion depicted by X⁻ may be selected from chloride, bromide, iodide, hydroxide, sulfate, nitrate, phosphate, acetate, trifluoroacetate, fumarate, citrate, tartrate, oxalate, succinate, mandelate, methanesulfonate or p-toluenesulfonate. In one embodiment the pharmaceutically acceptable anion X⁻ is bromide.

For purposes herein, the structural formula for the quaternary moiety (cation) of Compound (I) is also referred to as 4-[hydroxy(diphenyl)methyl]-1-{2-[(phenylmethyl)oxy]ethyl}-1-azoniabicyclo[2.2.2]octane or umeclidinium.

In one embodiment of the invention, Compound (I) is umeclidinium bromide.

Umeclidinium bromide is an investigational medicine described in Example 84 of WO2005/104745, which is incorporated by reference herein.

Compound (I), specifically umeclidinium bromide, has been the subject of studies in animal models and in humans, and has been found to be a long acting high-affinity pan-active muscarinic receptor antagonist which has potential for once-daily administration.

Pharmaceutical combination products of the present invention are considered to have potential in the treatment of inflammatory or respiratory tract diseases such as asthma, COPD, chronic bronchitis, pulmonary fibrosis, pulmonary emphysema, allergic rhinitis, small airways disease, bronchiectasis and cystic fibrosis.

COPD is a chronic disease characterised by airways obstruction and reduced maximum expiratory flow from the lungs that manifests as persistent daily symptoms, such as shortness of breath (dyspnoea), and limitation of the ability to perform daily activities or exertion. Furthermore, there are periodic exacerbations of the condition that result in worsening of the day-to-day symptoms and activity limitation, and can also lead to hospitalisation of the patient because of the severity of the worsening symptoms/limitation. In addition, there is a progressive decline in lung function (disease progression) over several years.

Bronchodilator treatment in COPD includes but is not necessarily limited to reducing symptoms, particularly dyspnoea, to allow a patient to undertake more daily activities and other activities that require exertion, and preventing exacerbations.

Asthma is a chronic condition, which is characterised by widespread, variable and reversible airflow obstruction. Symptoms include coughing, wheezing, breathlessness and/or a tight feeling in the chest. Asthma attacks are generally caused by exposure to a trigger, such as pollen, dust or other allergens, which causes constriction of the airways (bronchoconstriction). It will be appreciated that a subject suffering from a condition such as asthma, may variously from time to time display no overt symptoms of the condition, or may suffer from periodic attacks during which symptoms are displayed or may experience exacerbations or worsening of the condition. In this context the term 'treatment' is intended to encompass prevention of such periodic attacks or exacerbations of the existing condition. Such treatment may be referred to as 'maintenance treatment' or 'maintenance therapy'.

The amounts of umeclidinium, fluticasone propionate and salmeterol required to achieve a therapeutic effect will, of course, vary with the route of administration, the subject under treatment, the particular disorder or disease being treated, and the severity of the disease. In one embodiment, the route of administration is by inhalation via the mouth or nose. In a further embodiment, the route of administration is by inhalation via the mouth.

In one embodiment, umeclidinium may be administered by inhalation at a dose of from about 1 mcg to about 1000 mcg/daily, e.g. 100, 250 or 500 mcg per day (as umeclidinium bromide). In a further embodiment, umeclidinium may be administered by inhalation at a dose of 62.5 mcg or 125 mcg per day (as umeclidinium bromide). In general umeclidinium will be administered as a once-daily dose.

In a further embodiment, umeclidinium may be administered by inhalation, once-daily, at a dose of 62.5 mcg per day (as umeclidinium bromide).

In a further embodiment, umeclidinium may be administered by inhalation, once-daily, at a dose of 125 mcg per day (as umeclidinium bromide).

Fluticasone propionate may, for example, be administered by inhalation at a dose of from about 1 mcg to about 1000 mcg/day. In one embodiment, fluticasone propionate may be administered by inhalation at a dose of about 50, 100, 125, 250, or 500 mcg/day. In one embodiment, fluticasone propionate is administered twice daily. In one embodiment, fluticasone propionate may be administered by inhalation at a dose of 100 mcg/day. In another embodiment, fluticasone propionate may be administered by inhalation at a dose of 250 mcg/day. In yet a further embodiment, fluticasone propionate may be administered by inhalation at a dose of 500 mcg/day.

Salmeterol may, for example, be administered by inhalation at a dose of from about 1 mcg to 100 mcg/day. In one embodiment, salmeterol may be administered by inhalation at a dose of about 25 or 50 mcg/day (as salmeterol xinafoate). In one embodiment, salmeterol is administered twice daily. In one embodiment, salmeterol may be administered by inhalation at a dose of 25 mcg/day (as salmeterol xinafoate). In another embodiment, salmeterol may be administered by inhalation at a dose of 50 mcg/day (as salmeterol xinafoate).

In a further embodiment, the present invention provides a pharmaceutical combination product comprising umeclidinium at a dose of 62.5 mcg per day (as umeclidinium bromide), fluticasone propionate at a dose of 250 mcg/day and salmeterol at a dose of 50 mcg/day (as salmeterol xinafoate).

In a further embodiment, the present invention provides a pharmaceutical combination product comprising umeclidinium at a dose of 125 mcg per day (as umeclidinium bromide), fluticasone propionate at a dose of 250 mcg/day and salmeterol at a dose of 50 mcg/day (as salmeterol xinafoate).

The individual compounds of the pharmaceutical combination product as described herein may be administered either sequentially or simultaneously in separate or combined pharmaceutical formulations/compositions. Thus each compound may, for example, be formulated separately and presented in separate packs or devices, or said individually formulated components may be presented in a single pack or device. Where appropriate, the individual compounds may be admixed within the same formulation, and presented as a fixed pharmaceutical combination. In general such formulations will include one or more pharmaceutical carriers or excipients as described hereinafter, but combinations of the compounds without any excipients are also within the ambit of this invention. In one embodiment, Compound (I) is presented in a first dry powder composition, and b) fluticasone propionate and salmeterol xinafoate are presented in a second dry powder composition. In a further embodiment, said first dry powder composition containing Compound (I) is for delivery via a first dry powder inhaler, and said second dry powder composition containing fluticasone propionate and salmeterol xinafoate is for delivery via a second dry powder inhaler. In this embodiment, the two dry powder inhalers together comprise the pharmaceutical combination product.

The pharmaceutical combination products of the present invention may be in a form suitable for oral or nasal inhalation, and wherein administration is via one or more medicament dispensers selected from a reservoir dry powder inhaler, a unit-dose dry powder inhaler, a pre-metered multi-dose dry powder inhaler, a nasal inhaler or a pressurized metered dose inhaler.

In one embodiment, compound (I), fluticasone propionate and salmeterol xinafoate are presented in the same dry powder composition for delivery via a dry powder inhaler.

Powder compositions generally contain a powder mix for inhalation of the active ingredient and a suitable powder base (carrier/diluent/excipient substance) such as mono-, di or poly-saccharides (e.g. lactose or starch). In a further embodiment, each composition of a pharmaceutical combination product, and there may only be one if all of the three compounds are admixed together, contains a carrier. Lactose, such as anhydrous lactose or α-lactose monohydrate, is a suitable carrier. In one embodiment, the carrier is α-lactose monohydrate. Dry powder compositions may also include, in addition to the active ingredient and carrier, a further excipient (eg a ternary agent) such as a sugar ester, calcium stearate or magnesium stearate. Alternatively, the active ingredient may be presented without excipients. For the avoidance of doubt use of the term 'composition' or 'formulation' herein refers to the active ingredients either with or without excipients or carriers.

Powder compositions may further comprise a ternary agent. In one embodiment, dry powder compositions comprising compound (I) contain a ternary agent, such as magnesium stearate, In a further embodiment, magnesium stearate in present in an amount of about 0.6% w/w in dry powder compositions comprising compound (I).

The compositions may be prepared by any of the methods well known in the art of pharmacy. In general, said methods include the step of bringing the active ingredient(s) into association with the carrier which constitutes one or more accessory ingredients. In general the compositions are prepared by uniformly and intimately bringing into association the active ingredient with liquid carriers or finely divided solid carriers or both and then, if necessary, shaping the product into the desired composition.

The compositions may be presented in unit dosage form. Dry powder compositions for topical delivery to the lung by inhalation may, for example, be presented in capsules and cartridges of for example gelatine, or blisters of for example laminated aluminium foil, for use in an inhaler or insufflator. Packaging of the formulation may be suitable for unit dose or multi-dose delivery. As indicated above, the three compounds of the pharmaceutical combination products of the present invention may be formulated independently or in admixture. Said compounds may thus be incorporated in separate unit doses or may be combined in a single unit dose with or without additional excipients as deemed necessary.

In one embodiment, a composition suitable for inhaled administration may be incorporated into a plurality of sealed dose containers provided on medicament pack(s) mounted inside a suitable inhalation device. The containers may be rupturable, peelable or otherwise openable one-at-a-time and the doses of the dry powder composition administered by inhalation on a mouthpiece of the inhalation device, as known in the art. The medicament pack may take a number of different forms, for instance a disk-shape or an elongate strip. Representative inhalation devices are the DISKHALER™ and DISKUS™ devices, marketed by GlaxoSmithKline. The DISKUS™ inhalation device is, for example, described in GB 2242134A.

A dry powder inhalable composition, may also be provided as a bulk reservoir in an inhalation device, the device then being provided with a metering mechanism for metering a dose of the composition from the reservoir to an inhalation channel where the metered dose is able to be inhaled by a patient inhaling at a mouthpiece of the device. Exemplary marketed devices of this type are TURBUHALER™ of AstraZeneca, TWISTHALER™ of Schering and CLICKHALER™ of Innovata.

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ of GlaxoSmithKline and HANDIHALER™ of Boehringer Ingelheim.

A dry powder composition may also be presented in a delivery device which permits separate containment of Compound (I) and Compound (II) optionally in admixture with one or more excipients. Thus, for example, the individual compounds of the combination are administrable simultaneously but are stored separately, e.g. in separate pharmaceutical compositions, for example as described in WO 2003/061743 A1, WO 2007/012871 A1 and/or WO2007/068896. In one embodiment a delivery device permitting separate containment of actives is an inhaler device having two medicament packs in peelable blister strip form, each pack containing pre-metered doses in blister pockets arranged along its length. Said device has an internal indexing mechanism which, each time the device is actuated, peels opens a pocket of each strip and positions the packs so that each newly exposed dose of each pack is adjacent a manifold which communicates with a mouthpiece of the device. When the patient inhales at the mouthpiece, each dose is simultaneously drawn out of its associated pocket into the manifold and entrained via the mouthpiece into the patient's respiratory tract. Thus, each time the device is used, the patient is administered a combination therapy consisting of a dose from each medicament pack. A further device that permits separate containment of different compounds is DUGHALER™ of Innovata.

The present invention further provides a pharmaceutical combination product for inhaled administration comprising umeclidinium bromide, fluticasone propionate and salmeterol xinafoate, wherein umeclidinium bromide is formulated with lactose and magnesium stearate (0.6% w/w) in a first composition, and fluticasone propionate and salmeterol xinafoate are formulated together with lactose in a second composition, and wherein each composition is held in a separate dry powder inhaler for sequential or simultaneous administration.

In a further embodiment, the present invention provides a dry powder inhaler (Inhaler 1) comprising two compositions presented separately, wherein a first composition comprises:
  i. umeclidinium bromide,
  ii. lactose, and iii. magnesium stearate at an amount of about 0.6% w/w based on the total weight of the first composition;
and a second composition comprises
i. fluticasone propionate,
ii. salmeterol xinafoate, and
iii. lactose.

In a further embodiment, the present invention provides Inhaler 1 wherein each composition is in unit dose form, such as a blister In a further embodiment, the present invention provides Inhaler 1 wherein umeclidinium is present in an amount of about 62.5 mcg/dose or 125 mcg/dose (as umeclidinium bromide).

In a further embodiment, the present invention provides Inhaler 1 wherein fluticasone propionate is present in an amount of about 250 mcg/dose.

In a further embodiment, the present invention provides Inhaler 1 wherein salmeterol is present in an amount of about 50 mcg/dose (as salmeterol xinafoate).

Spray compositions for inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the pharmaceutical product and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid, lecithin or an oligolactic acid derivative e.g. as described in WO94/21229 and WO98/34596 and/or cosolvents e.g. ethanol. Pressurised formulations will generally be retained in a canister (e.g. an aluminium canister) closed with a valve (e.g. a metering valve) and fitted into an actuator provided with a mouthpiece.

Where appropriate compositions according to the invention may be buffered by the addition of suitable buffering agents.

Active ingredients for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means e.g. by micronization. The desired fraction may be separated out by air classification or sieving. Preferably, the particles will be crystalline.

Dry powder compositions according to the invention may comprise a carrier. The carrier when it is lactose e.g. α-lactose monohydrate, may form from about 91 to about 99%, e.g. 97.7-99.0% or 91.0-99.2% by weight of the formulation. In general, the particle size of the carrier, for example lactose, will be much greater than the inhaled medicament within the present invention. When the carrier is lactose it will typically be present as milled lactose, having a MMD (mass median diameter) of 60-90 μm.

The lactose component may comprise a fine lactose fraction. The 'fine' lactose fraction is defined as the fraction of lactose having a particle size of less than 7 μm, such as less than 6 μm, for example less than 5 μm. The particle size of the 'fine' lactose fraction may be less than 4.5 μm. The fine lactose fraction, if present, may comprise 2 to 10% by weight of the total lactose component, such as 3 to 6% by weight fine lactose, for example 4.5% by weight fine lactose.

Magnesium stearate, if present in the composition, is generally used in an amount of about 0.2 to 2%, e.g. 0.6 to 2% or 0.5 to 1.75%, e.g. 0.6%, 0.75%, 1%, 1.25% or 1.5% w/w, based on the total weight of the composition. The magnesium stearate will typically have a particle size in the range 1 to 50 μm, and more particularly 1-20 μm, e.g. 1-10 μm. Commercial sources of magnesium stearate include Peter Greven, Covidien/Mallinckodt and FACI.

Solutions for inhalation by nebulization may be formulated with an aqueous vehicle with the addition of agents such as acid or alkali, buffer salts, isotonicity adjusting agents or antimicrobials. They may be sterilized by filtration or heating in an autoclave, or presented as a non-sterile product.

Clinical Studies
Umeclidinium Bromide

Umeclidinium bromide has been found to be an effective long-acting potent, pan-active anti-muscarinic bronchodilator which demonstrates slow reversibility at the human M3 receptor in vitro and long duration of action in vivo when administered directly to the lungs in pre-clinical models. The long duration of action of this compound identified using in vitro models, when administered via inhalation in animals, and subsequently in early phase studies in healthy volunteers and COPD subjects supports the potential for use of this compound as a once daily bronchodilator for COPD.

Several clinical pharmacology studies have been conducted using umeclidinium bromide in both healthy volunteers and COPD patients to investigate the safety, tolerability, pharmacokinetics and pharmacodynamics of this compound. The bronchodilatory effects and duration of action of single inhaled doses of this compound as measured by plethysmography ($sG_{aw}$, $R_{aw}$) and spirometry ($FEV_1$) were assessed in some of the above noted studies. These studies showed clinically relevant bronchodilation and 24 h duration of action for the compound.

In one such study, designed to evaluate the safety, efficacy and pharmacokinetics of umeclidinium bromide in subjects with COPD, five once-daily doses of umeclidinium (62.5 mcg, 125 mcg, 250 mcg, 500 mcg and 1000 mcg as umeclidinium bromide), taken over a 14-day treatment period, produced statistically significant improvements in pulmonary function compared to placebo. All once-daily doses showed numerically greater improvement in trough $FEV_1$ than the open label tiotropium active control (18 mcg once-daily). In addition, this study confirmed that umeclidinium bromide has a once-daily profile.

A further study evaluated the efficacy and safety of three doses of umeclidinium (125 mcg, 250 mcg and 500 mcg as umeclidinium bromide) administered once-daily via a dry powder inhaler over a 28 day period in subjects with COPD. This study confirmed that umeclidinium bromide appears to be safe and efficacious, maintaining significant bronchodilation over twenty four hours.

Combination Therapy

A 12-week study in patients with COPD evaluated the efficacy and safety of the addition of:

umeclidinium inhalation powder (62.5 mcg as umeclidinium bromide) once-daily to fluticasone propionate/salmeterol (FSC)(250/50 mcg as salmeterol xinafoate) twice-daily, umeclidinium inhalation powder (125 mcg as umeclidinium bromide) once-daily to fluticasone propionate/salmeterol (FSC)(250/50 mcg as salmeterol xinafoate) twice-daily versus placebo to fluticasone propionate/salmeterol (250/50 mcg as salmeterol xinafoate) twice-daily.

Results:

Compared with placebo+FSC, both doses of UMEC+FSC produced statistically significant and clinically meaningful improvements in trough $FEV_1$ at Day 85 (62.5 mcg=0.147 L; 125 mcg=0.138 L) and WM $FEV_1$ at Day 84 (62.5 mcg=0.164 L; 125 mcg=0.160 L; both $p<0.001$). During Weeks 1-12, patients in the UMEC+FSC treatment groups experienced more rescue-free days and greater mean changes from baseline in rescue-free days (62.5 mcg=59.4% and 13.3 days; 125 mcg=56.1% and 11.1 days) compared with placebo+FSC (49.7% and 4.9 days). For both UMEC+FSC groups rescue albuterol use was reduced by 0.3 puffs/day compared with placebo+FSC (both $p<0.05$).

Conclusions:

The addition of once-daily UMEC (62.5 or 125 mcg) to twice-daily FSC (250/50 mcg) was well tolerated and resulted in improvements in lung function and rescue use compared with placebo+FSC in patients with COPD.

Pharmaceutical Formulations

Preparation of Blends

Umeclidinium Bromide

Pharmaceutical grade α-lactose monohydrate, sourced from DMV Fronterra Excipients, complying with the requirements of Ph.Eur/USNF may be used. Before use, the α-lactose monohydrate may be sieved through a coarse screen (for example with a mesh size 500 or 800 microns). The level of fines in the α-lactose monohydrate, which can be measured by Sympatec, may be 4.5% w/w less than 4.5 micron.

Umeclidinium bromide is micronised before use in an APTM microniser to give a mass median diameter of 1 to 5 microns, such as 2 to 5 microns.

Pharmaceutical grade magnesium stearate, sourced from Peter Greven, complying with the requirements of Ph.Eur/USNF may be used as supplied with a mass median particle size of 8 to 12 microns.

Blend A

Lactose monohydrate may be passed through a sieve and then combined with magnesium stearate and blended using either a high shear mixer (a QMM, PMA or TRV series mixer, such as TRV25 or TRV65) or a low shear tumbling blender (a Turbula mixer) to provide a magnesium stearate/lactose premix, hereinafter referred to as blend A.

Blend B

Final blend B may be obtained as follows. An quantity of blend A and umeclidinium bromide may be screened, for example using a COMIL™, and then blended with the remaining blend A using either a high shear mixer (a QMM, PMA or TRV series mixer, such as TRV25 or TRV65) or a low shear tumbling blender (a Turbula mixer).

Representative Batch Formula for Umeclidinium Bromide Powder Blend (62.5 Microgram Per Blister)

| Ingredient | Quantity |
| --- | --- |
| Micronised Umeclidinium bromide | 74.1 g |
| Magnesium Stearate | 75 g |
| Lactose Monohydrate | To 12.5 kg |

Note:
74.1 g of umeclidinium bromide is equivalent to 62.5 g of the free cation, umeclidinium. The quantity of umeclidinium bromide added may be adjusted to reflect the assigned purity of the input drug substance.

Representative Batch Formula for Umeclidinium Bromide Powder Blend (125 Microgram Per Blister)

| Ingredient | Quantity |
| --- | --- |
| Micronised Umeclidinium bromide | 148.3 g |
| Magnesium Stearate | 75 g |
| Lactose Monohydrate | To 12.5 kg |

Note:
148.3 g of umeclidinium bromide is equivalent to 125 g of the free cation, umeclidinium. The quantity of umeclidinium bromide added may be adjusted to reflect the assigned purity of the input drug substance.

Blending Parameters (Using a TRV25, 12.5 kg Scale)

| Blend | Time (mins) | Approximate Speed (rpm) |
| --- | --- | --- |
| A | 6 | 460 |
| B | 10 | 590 |

Blister Strip Preparation

The blended composition may then be transferred into blister strips (typical nominal mean quantity of blend per blister is 12.5-13.5 mg) of the type generally used for the supply of dry powder for inhalation and the blister strips were sealed in the customary fashion.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

The invention claimed is:

1. A pharmaceutical combination product comprising:
   a) umeclidinium bromide;
   b) fluticasone propionate; and
   c) salmeterol xinafoate.

2. A product according to claim 1, wherein the pharmaceutical combination product is suitable for administration by inhalation via one or more medicament dispensers selected from a reservoir dry powder inhaler, a unit-dose dry powder inhaler, a pre-metered multi-dose dry powder inhaler, a nasal inhaler or a pressurized metered dose inhaler.

3. A product according to claim 2, wherein a) umeclidinium bromide is presented in a first dry powder composition, and b) fluticasone propionate and salmeterol xinafoate are presented in a second dry powder composition.

4. A product according to claim 3, wherein the first dry powder composition is for delivery via a first dry powder inhaler and the second dry powder composition is for delivery via a second dry powder inhaler.

5. A product according to claim 3, wherein umeclidinium bromide, fluticasone propionate and salmeterol xinafoate are presented in the same dry powder composition for delivery via a dry powder inhaler.

6. A product according to claim 3, wherein each dry powder composition contains lactose.

7. A product according to claim 3, wherein a dry composition comprising umeclidinium bromide contains magnesium stearate in an amount of about 0.6% w/w.

8. A product according to claim 3, wherein each dry powder composition is presented in unit dose form, wherein the unit dose form is in a capsule, cartridge or blister pack.

9. A product according to claim 1, wherein umeclidinium bromide is present in an amount of about 125 mcg/dose or about 62.5 mcg/dose.

10. A product according to claim 1, wherein fluticasone propionate is present in an amount of about 100, 250 or 500 mcg/dose.

11. A product according to claim 1, wherein salmeterol xinafoate is present in an amount of about 50 mcg/dose.

12. A dry powder inhaler containing a product as defined in claim 1.

13. A pharmaceutical combination product comprising:
a) umeclidinium bromide in an amount of about 125 mcg/dose or about 62.5 mcg/dose,
b) fluticasone propionate in an amount of about 100, about 250 or about 500 mcg/dose, and
c) salmeterol xinafoate in an amount of about 50 mcg/dose.

14. A product according to claim 13, wherein the pharmaceutical combination product is suitable for administration by inhalation via one or more medicament dispensers selected from a reservoir dry powder inhaler, a unit-dose dry powder inhaler, a pre-metered multi-dose dry powder inhaler, a nasal inhaler or a pressurized metered dose inhaler.

15. A product according to claim 14, wherein a) umeclidinium bromide is presented in a first dry powder composition, and b) fluticasone propionate and salmeterol xinafoate are presented in a second dry powder composition.

16. A product according to claim 15, wherein the first dry powder composition is for delivery via a first dry powder inhaler and the second dry powder composition is for delivery via a second dry powder inhaler.

17. A product according to claim 15, wherein umeclidinium bromide, fluticasone propionate and salmeterol xinafoate are presented in the same dry powder composition for delivery via a dry powder inhaler.

18. A product according to claim 15, wherein each dry powder composition contains lactose.

19. A product according to claim 15, wherein a dry composition comprising umeclidinium bromide contains magnesium stearate in an amount of about 0.6% w/w.

20. A product according to claim 13, wherein each dry powder composition is presented in unit dose form, wherein the unit dose form is in a capsule, cartridge or blister pack.

21. A dry powder inhaler containing a product as defined in claim 13.

* * * * *